United States Patent
Burgess

[11] Patent Number: 5,171,147
[45] Date of Patent: Dec. 15, 1992

[54] DENTAL BRIDGE

[76] Inventor: Richard J. Burgess, 53A Dutton Terrace, Medindie, South Australia, 5081, Australia

[21] Appl. No.: 692,237

[22] Filed: Apr. 26, 1991

[30] Foreign Application Priority Data

Apr. 30, 1990 [AU] Australia ............... PJ9870

[51] Int. Cl.$^5$ .............................. A61C 13/12
[52] U.S. Cl. ..................... 433/180; 433/181; 433/202.1; 433/212.1
[58] Field of Search ............. 433/180, 181, 212.1, 433/222.1, 199.1, 202.1, 191, 215

[56] References Cited

U.S. PATENT DOCUMENTS

| | | | |
|---|---|---|---|
| 1,436,016 | 11/1922 | DeNise | 433/180 |
| 4,029,632 | 6/1977 | Gross et al. | 433/199.1 |
| 4,312,917 | 1/1982 | Hawley | 428/375 |
| 4,717,341 | 1/1988 | Goldberg et al. | 433/9 |
| 4,820,157 | 4/1989 | Salvo | 433/215 |
| 4,894,012 | 1/1990 | Goldberg et al. | 433/6 |
| 5,007,836 | 4/1991 | Gayso | 433/181 |

FOREIGN PATENT DOCUMENTS

| | | |
|---|---|---|
| 45903/79 | 10/1979 | Australia . |
| 54730/80 | 8/1980 | Australia . |
| 51156/85 | 12/1985 | Australia . |
| 71544/87 | 10/1987 | Australia . |
| 8904640 | 6/1989 | PCT Int'l Appl. . |

*Primary Examiner*—Cary E. O'Connor
*Attorney, Agent, or Firm*—Edward W. Callan

[57] ABSTRACT

A dental bridge having the general configuration of a tooth or teeth, with projecting lateral arms or wings which are gradually tapering lateral extensions of the bridge itself, conterminous with the bridge and formed of the same material as the bridge. The bridge is molded from a heat-polymerizable matrix formed from a resin selected from the group consisting of methacrylates, acrylates, and mixtures thereof. The matrix includes 60-80 wt % of inorganic filler(s). The lateral arms or wings use chemical bonding to engage with the proximal and/or occlusal surfaces of the teeth on either side of the gap in which the bridge is to be inserted.

11 Claims, 1 Drawing Sheet

DENTAL BRIDGE

BACKGROUND TO THE INVENTION

The present invention relates primarily to dental bridges, i.e. devices which enable the replacement of a tooth or teeth missing from the natural dentition of a human or other animal. They consist of a strong core material bonded to the proximal teeth on either side of the gap caused by the missing tooth or teeth. A similar core material can be utilised in other dental applications, e.g. for dental fillings and other dental inserts.

SUMMARY OF THE INVENTION

The present invention provides a dental bridge having the general configuration of a tooth or teeth, with projecting lateral arms or wings which are gradually tapering lateral extensions of the bridge itself, conterminous with the bridge and formed of the same material as the bridge, said lateral arms or wings being engageable using chemical bonding, and without the use of any mechanical anchoring device with the proximal and/or occlusal surfaces of the teeth on either side of the gap in which said bridge is to be inserted.

DETAILED DESCRIPTION OF THE INVENTION

The base resins used to manufacture the present dental inserts are methacrylate and/or acrylate resins, e.g. urethane dimethacrylate, Bis/GMA or ethoxylated Bis phenol A dimethacrylate. In fact, any monofunctional or multifunctional methacrylate or acrylate may be used. The abovementioned resins are viscous liquids at room temperature, and it may be necessary to reduce their viscosity with compatible, copolymerizable diluents. The lower viscosity resins achieved with such diluents have the following advantages:

(a) They provide a paste having unique rheological properties.
(b) It is easier to dissolve active ingredients.
(c) The addition of functional (or reactive) diluents has the added advantage of promoting polymer crosslinking and enhancing the strength of the composition.

Suitable diluents include mono- or multi-functional methacrylates having viscosities ranging from 1 to 100 CP.

Preferred functional diluents are triethylene glycol dimethacrylate and 1,6-hexane-diol dimethacrylate. The diluent may be present in the range of 20 to 50 wt % of total resin, and preferably 30 to 50 wt % of total resin.

The resin matrix may also include other conventional additives, according to requirements, such as:

(a) UV-absorbers,
(b) free radical scavengers, and
(c) initiators for polymerization.

(a) The purpose of the UV-absorber is to protect the final polymer product from UV-induced deterioration and discoloration. UV-absorbers, such as UV-9 supplied by the Cyanamid Corporation, convert the harmful UV rays of the sun into harmless heat through internal reactions. Typical addition rates for UV-absorbers are in the range of 0.1 to 0.5 wt % of total resin.

(b) Free radical scavengers may be included in the formulation in order to improve the shelf life of the paste, prior to moulding. These scavengers (sometimes referred to as "inhibitors") work by combining with active free radicals, which are produced by accidental exposure to heat. The scavengers deactivate the free radicals before they can initiate a chain reaction. Butylated hydroxy toluene (or BHT) is one such scavenger, and is typically added in the range of 200 to 500 parts per million (by weight).

(c) The core material is essentially a heat-polymerized polymer, preferably cured in an injection moulding machine at a temperature of 70° C. to 120° C. (preferably 80° C. to 110° C.). Although other peroxide initiators (such as lauryl peroxide or mixtures of peroxides) are also suitable, benzoyl peroxide is the preferred initiator. Suitable concentrations for peroxide initiators range from 0.1 to 2 wt % of the polymer.

A high concentration of inorganic fillers is added to the resin matrix of the core. The inorganic fillers improve strength and wear resistance. The unique rheological properties of the paste allow flow suitable for injection moulding processes. The inorganic fillers preferably comprise a blend of microfine small particles and short fibres.

The microfine small particle filler has a particle size in the range of 1 to 50 microns (preferably 1 to 15 microns). The concentration of microfine small particle filler may be 10 to 50 wt % of total filler loading, and is preferably 10 to 30 wt % of total filler.

Preferred microfine small particle fillers are pyrogenic or precipitated silica in the range of 10 to 20 wt % of total filler loading. Other suitable microfine fillers include:

(i) Two phase randomly shaped strontium Borosilicate glass. This glass is X-ray opaque.
(ii) Barium alumino-silicate glass, which is also X-ray opaque.
(iii) Lithium alumino-silicate, which has a negative coefficient of thermal expansion.
(iv) Pure quartz.
(v) Fluoride-containing glass.

The short fibre fillers suitable for the hybrid core material of this invention may be glass fibres, typically having a diameter of 8 to 20 microns and a length of 20 to 100 microns.

Preferable ranges for the diameter and length are 10 to 15 microns and 30 to 40 microns, respectively. The abovementioned fibre dimensions are readily achieved by centrifugal milling of short fibres having initial dimensions of 0.3 to 0.8 mm, preferably 0.3 to 0.5 mm. A particularly suitable glass fibre composition is manufactured from two phase strontium Borosilicate glass, having one phase acid-soluble to enable acid etching and improved mechanical interlocking for the reinforcing process.

Short fibres preferably comprise 4 to 15 wt % of total filler loading, and most preferably 4 to 10 wt % of total filler.

The reinforcing fillers of the present invention may be coupled with functional silanes, designed to achieve physiochemical adhesion of the fillers to the resin matrix and thus enhance the reinforcement effect. In addition to the reinforcement effect, a silane coating would make the filler:

(i) Hydrophobic and reduce water sorption. Reduced water sorption would improve the hydrolytic stability of the resin matrix.

(ii) Organophilic, i.e. wetting with the resin and mixing is much easier, thus enabling high filler loadings.

The total filler loading of the composition is preferably within the range of 60 to 90 wt % of total core material, and most preferably within the range of 75 to 85 wt % of total core material.

The resin matrix contains an optimum blend of small particle and short fibre fillers, and is cured by heat under pressure. This unique curing method produces an extremely strong core material.

The high filler loading and the heat processing under pressure ensures production of a very dense non-porous material with the following characteristics:
  (a) Very high flexural and compressive strength.
  (b) Permanent high gloss after polishing.
  (c) High abrasive resistance.
  (d) Very low water sorption.

This specially-developed methacrylate and/or acrylate based resin has high water repellency, chemical resistance to oral fluids, resistance to plaque formation and excellent mechanical properties and colour stability.

The hybrid core material of the present invention is entirely compatible with most visible light cured, UV cured and chemically cured composites. It is also compatible with other heat-cured composites, such as inlay/onlay materials. This compatibility allows chemical bonding of the hybrid core material to these materials. It can therefore be reshaped and colour adjusted using e.g. regular light cured filling materials.

The hybrid core material is preferably formed and moulded by a simple injection moulding process, using a combination of heat (e.g. temperatures of 70°-120° C., preferably 80°-110° C.) and pressure, to cure the material. One of the most important characteristics of the product is the extra strength resulting from the pressure conditions existing during the polymerization process.

Pre-shaped dental bridges made out of the hybrid core material of the present invention are void-free because of the pressure conditions of the mixing process and the unique method of injecting the product into the die.

The accompanying drawings illustrate a typical dental bridge which is illustrative, but not restrictive, of the present invention.

Figure 1:
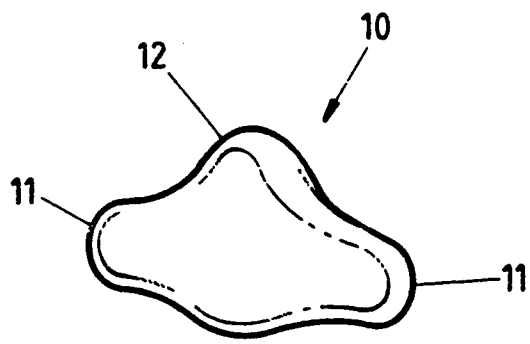
FIG. 1 is a rear view of the dental bridge.

Various types of dental bridge may be manufactured. In all cases, the dental bridge 10 has the general configuration of the missing tooth or teeth, with projecting lateral arms or wings 11 to engage with the proximal and/or occlusal surfaces of the teeth 14 on either side of the gap. That is, the lateral arms or wings 11 may engage with only the proximal surfaces of the adjacent teeth 14, with only the occlusal surfaces, or with a combination of proximal and occlusal surfaces. The various types are as follows:

(a) Standard Type.
  This is for replacing premolar or canine teeth. It has an ovoid shape in the central space area. Height approx. 4-8 mm, width approx. 3-5 mm and thickness approx. 3-5 mm. An arm of hard-core material extends on either side.

(b) Anterior Type.
  This is for replacing anterior incisors. The core is more flattened, with about a 2 mm thickness. The arms are more wing-like and flattened, with a thickness of approx. 1-2 mm.

Canine Type.
  The core is similar to the Standard Type, but shaped similar to a canine crown.

(d) Double Type.
  This consists of two ovoid cores, each of which is similar to the Standard Type.

(e) Molar Type.
  This has a bigger ovoid area.

PREPARATION OF DENTAL CAVITY (a) For Premolar or Molar Teeth

If teeth 14 adjacent to the gap are sound, an occlusal channel 15 (preferably a horizontal channel having a depth of approx. 2-3 mm) is cut or drilled into the proximal surfaces of said teeth. These channels are designed to accommodate the arms of the dental bridge.

If a filling is already present in the proximal surface of an adjacent tooth, it should be removed, a suitable lining inserted (if necessary), and the cavity filled e.g. with glass ionomer or light-cured composite, but leaving the required shallow occlusal channel 15 open.

The dental bridge 10 is trimmed to fit the space, and its arms 11 are trimmed to fit the occlusal channels. The dental bridge is preferably over-extended, because it is easy to trim off excess material.

Figure 2:
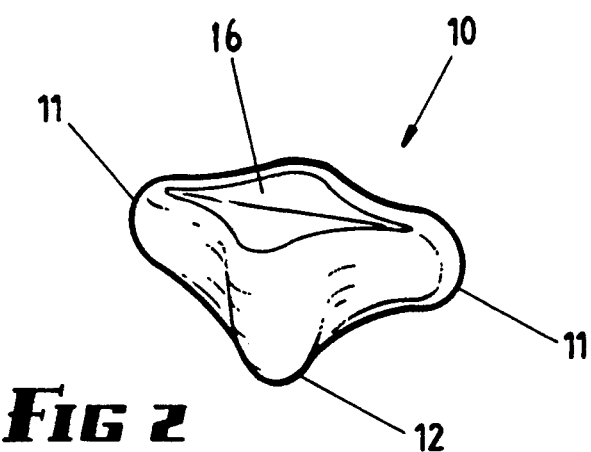
FIG. 2 is a perspective view of the dental bridge.
Figure 3:
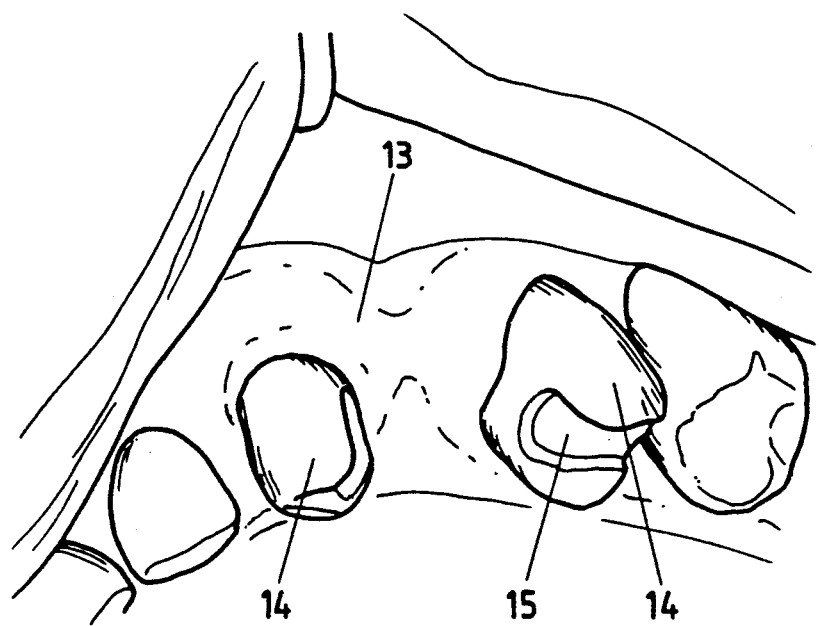
FIG. 3 is a perspective view, illustrating preparation of adjacent teeth for insertion of the bridge.

The arms 11 of the dental bridge can be set in the occlusal channels 15 with either glass ionomer or light cured composite. Surface 12 of the bridge (as labelled in FIGS. 1 and 2) contacts the gum 13 of the patient, whereas the biting surface of the bridge is labelled 16.

The remaining cavity space can be filled e.g. with light cured composite. The inserted bridge 10 can then be given a final trim and polish.

(b) For Canines and Anterior Teeth

In this case, the dental bridge has wings 11, and the backs of the adjacent teeth 14 are ground to accept these wings. Alternatively a groove 15 can be cut in the side of each tooth adjoining the space. The bridge is made with side flanges 11 which fit into the grooves.

(c) For Front Incisors

For replacement of front incisors, about 0.5 to 1 mm is removed from lingual or proximal teeth in an approx. 3 mm arc adjacent to the space. The dental bridge 10 is trimmed to fit in snugly. The teeth in the prepared area are etched, washed, dried and then a bonding agent is applied. A similar bonding agent is also placed on the wings 11 of the bridge, with any excess being blown off. Light cure composite is then added to the wings 11, and the wings are seated in position. The composite is hardened with light. The front of the bridge is then built up with colour-matched composite. The bridge is trimmed, and the occlusion checked. The inserted bridge is then finished and polished.

In all cases, the occlusion is checked, after the bridge has been inserted.

To ensure that the occlusion is clear, the bridge is eased or (where indicated) high cusps on the opposing teeth are reduced.

Most occlusions with an even bite are suitable for the dental bridge. However, the bridge may be contra-indicated in cases of heavy over-bite.

The pontic can be built up using light-cured composite.

Colour can also be adjusted by adding the appropriate shade of light-cured composite.

Advantages of the present dental bridge are:

(a) It can be prepared and inserted quickly (in one appointment, if so required).
(b) It is simple. No laboratory processing is necessary.
(c) Aesthetic considerations. It forms a most satisfactory cosmetic restoration.
(d) High flexural and compressive strength.
(e) It can easily be colour-matched.
(f) It forms a viable alternative to a removable prosthetic appliance.
(g) It is a cheaply fixed device (considerably cheaper than a porcelain replacement).
(h) It is X-ray opaque.

In order to further illustrate the present invention, the following examples are provided. Example 1 illustrates various methods of bridge preparation. Examples 2 to 4 illustrate suitable core compositions.

EXAMPLE 1

Bridge Preparation (a) Indirect Method

1. After preparing the tooth cavities, as outlined previously, an impression is taken with a suitable dental impression material in a rigid impression tray. A polysiloxane, poly-ether, or similar rubber base material is most satisfactory. Alginate impressions are suitable where distortion is unlikely to occur and the impression can be cast fairly quickly.

An impression should be taken of the opposing dentition to check the bite.

2. The dental bridge is applied to the cast and trimmed with burs and discs until it fits into the space and the cavity preparations in the adjacent teeth.

3. The full contour of the pontic tooth is built up with the desired light cured filling material. The pontic can be fully built up and the bite checked against the opposing cast.

Final polishing of the pontic can be completed at this stage.

The dental bridge is then inserted and fixed in the mouth at the next appointment.

(b) Direct Method

1. A suitable dental bridge is selected and applied to the prepared teeth in the mouth.
2. The dental bridge is trimmed with burs and discs until it seats satisfactorily in the teeth and space.
3. The dental bridge is set in the tooth cavities with glass ionomer or light cured composite.
4. The occlusion is checked carefully and gently and the bite eased until clear.
5. The proximal teeth are filled with light cured composite and the occlusion is checked again.
6. The facings, occlusal and lingual aspects are built up with a suitable light cured composite in the chosen blending colour. Preformed clear (celluloid style crown patterns are most helpful.
7. Occlusion and clear bite are checked.
8. The finished bridge is polished.

EXAMPLE 2

| | Parts by weight |
|---|---|
| (a) Resin Composition | |
| Urethane Dimethacrylate | 70 |
| 1.6-Hexane-diol Dimethacrylate | 30 |
| BHT | 250 (PPM) |
| UV-9 | 0.1 |
| Benzoyl Peroxide | 1.0 |
| (b) Paste Composition | |
| Resin | 100 |
| Barium Glass (10 micron) | 80 |
| Pyrogenic Silica (40 nm) | 40 |
| Strontium Fibre 12 micron diameter 30 micron length | 80 |
| Wetting agent (anionic surfactant) | 200 PPM based on total filler |

The above formula was heat polymerized in an injection moulding machine (used as a compression moulding machine) at 100° C. for five minutes. Flexural strength of the resultant polymer was 150 MPa.

EXAMPLE 3

| | Parts by weight |
|---|---|
| (a) Resin Composition | |
| Bis/GMA | 65 |
| Triethylene glycol Dimethacrylate | 35 |
| BHT | 100 (PPM) |
| UV-9 | 0.5 |
| Lauryl peroxide | 0.7 |
| (b) Past Composition | |
| Resin | 100 |
| Strontium Borosilicate Glass (20 micron) | 90 |
| Pyrogenic silica (40 nm) | 30 |
| Strontium fibre 12 micron diameter 30 micron length | 80 |
| Wetting agent (anionic surfactant) | 200 PPM of total filler |
| Iron oxide pigment | 200 PPM of total filler |

The above formula was heat cured at 90° C. and 200 Psi pressure in an injection moulding machine for three minutes. Flexural strength of the resultant product was 170 MPa.

EXAMPLE 4

| | Parts by weight |
|---|---|
| Resin A2 | 100 |
| Quartz 25 micron | 90 |
| Pyrogenic silica (40 nm) | 10 |
| Strontium fibre 12 micron diameter 30 micron length | 100 |
| Wetting agent (anionic surfactant) | 0.1 |
| Iron oxide pigment | 0.1 |

The above formula was heat cured at 80° C. and 100 Psi for five minutes. Flexural strength of the resultant product was 200 MPa.

While the present invention has been described in terms of preferred embodiments in order to facilitate better understanding of the invention, it should be appreciated that various modifications can be made without departing from the spirit and scope of the invention, as indicated by the accompanying claims. Therefore, the invention should be understood to include all such modifications within its scope.

We claim:

1. A dental bridge having the general configuration of a tooth or teeth, with projecting lateral arms or wings which are gradually tapering lateral extensions of the bridge itself, conterminous with the bridge and formed of the same material as the bridge, said lateral arms or wings being engageable using chemical bonding, and without the use of any mechanical anchoring device, with the proximal and/or occlusal surfaces of the teeth on either side of the gap in which said bridge is to be inserted.

2. A dental bridge having the general configuration of a tooth or teeth, with projecting lateral arms or wings which are gradually tapering lateral extensions of the bridge itself, conterminous with the bridge and formed of the same material as the bridge, said lateral arms or wings being engageable using chemical bonding, and without the use of any mechanical anchoring device, with the proximal and/or occlusal surfaces of the teeth on either side of the gap in which said bridge is to be inserted, said dental bridge being moulded from a heat-polymerizable matrix formed from a resin selected from the group consisting of methacrylates, acrylates and mixtures thereof, said matrix comprising 60 to 90 wt % of inorganic filler(s).

3. A dental bridge according to claim 2, comprising 75 to 85 wt % of inorganic filler(s).

4. A dental bridge according to claim 2, wherein the resin is urethane dimethacrylate, Bis/GMA or ethoxylated Bis phenol A dimethacrylate.

5. A dental bridge according to claim 2, wherein the filler(s) comprise microfine small particles, having a particle size in the range of 1 to 50 microns.

6. A dental bridge according to claim 5, wherein the microfine small particle filler is selected from the group consisting of pyrogenic silica, precipitated silica, strontium Borosilicate glass, barium alumino-silicate glass, lithium alumino-silicate, quartz and fluoride-containing glass.

7. A dental bridge according to claim 5, wherein the microfine small particles amount to 10 to 50 wt % of total filler loading.

8. A dental bridge according to claim 2, wherein the filler(s) comprise short fibres having a diameter of 8 to 20 microns and a length of 20 to 100 microns.

9. A dental bridge according to claim 8, wherein said short fibres are formed from glass.

10. A dental bridge according to claim 8, wherein said short fibres amount to 4 to 15 wt % of total filler loading.

11. A dental bridge according to claim 2, further comprising at least one additive selected from the group consisting of UV-absorbers, free radical scavengers and initiators for polymerization.